United States Patent

Steckelberg et al.

Patent Number: 5,414,128
Date of Patent: May 9, 1995

[54] PROCESS FOR THE PREPARATION OF N-SUBSTITUTED NITRO-P-PHENYLENEDIAMINES

[75] Inventors: Willi Steckelberg, Hofheim/Ts.; Rolf Müller, Karben; Peter Koch, Obertshausen, all of Germany

[73] Assignee: Cassella AG, Frankfurt, Germany

[21] Appl. No.: 984,976

[22] Filed: Dec. 3, 1992

[30] Foreign Application Priority Data

Dec. 14, 1991 [DE] Germany ............ 41 41 369.5

[51] Int. Cl.⁶ .......................... C07C 209/10
[52] U.S. Cl. .................... 564/406; 564/441; 564/395
[58] Field of Search ............ 564/406, 399, 405, 441

[56] References Cited

FOREIGN PATENT DOCUMENTS 0040762 12/1981 European Pat. Off.
0226973 7/1987 European Pat. Off.
1094452 5/1955 France.
1206491 9/1970 United Kingdom.
1455207 11/1974 United Kingdom.
2164656 9/1984 United Kingdom.

OTHER PUBLICATIONS

*Advanced Organic Chemistry*, Reactions, Mechanisms, and Structure, Second Edition, p. 592, (1977).

Primary Examiner—Glennon H. Hollrah
Assistant Examiner—Brian M. Burn
Attorney, Agent, or Firm—Connolly and Hutz

[57] ABSTRACT

The present invention relates to a process for the preparation of compounds of the general formula I

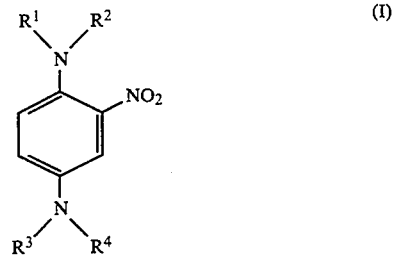

by reaction of compounds of the general formula II

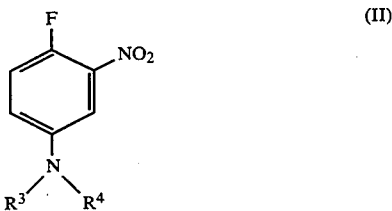

with amines of the general formula III

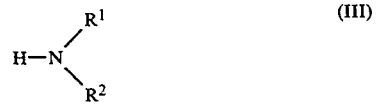

wherein $R^1$ and $R^2$ independently of one another denote hydrogen, $(C_1-C_4)$-alkyl, $C_1-C_4$)-hydroxyalkyl or $(C_5-C_6)$-cycloalkyl, or, together with the nitrogen atom carrying them, form $(C_4-C_6)$-heterocyclyl and $R^3$ and $R^4$ independently of one another denote hydrogen, $(C_1-C_4)$-alkyl, $(C_1-C_4)$-hydroxyalkyl, $(C_1-C_2)$-alkylcarbonyl or tosyl.

19 Claims, No Drawings

PROCESS FOR THE PREPARATION OF N-SUBSTITUTED NITRO-P-PHENYLENEDIAMINES

The present invention relates to a process for the preparation of N-substituted nitro-p-phenylenediamines. N-substituted nitro-p-phenylenediamines are known and are used as dyestuffs, in particular for dyeing human hair (see, for example, U.S. Pat. Nos. 27 50 327, 3,088,978, 3,168,442, 3,088,877, 3,119,867, 3,088,878, 3,274,249, GB 1,206,491, EP 226 973 and DE 35 34 369).

Several processes for their preparation are already known in the literature.

For example, according to GB 955,743 and U.S. Pat. No. 3,168,442, $N^1$-(hydroxyalkyl)-2-nitro-1,4-phenylenediamines can be obtained by partial reduction of 2,4-dinitro-1-hydroxyalkylaminobenzenes. The disadvantage of this process is that isomer mixtures and completely reduced triaminobenzenes are formed as by-products, so that separation presents difficulties.

According to DE 39 31 836, 2-nitro-1,4-phenylenediamine is first acetylated in the 4-position, the 1-position is then converted into the corresponding carbamate with a chloroalkyl chloroformate, and this carbamate is rearranged and hydrolysed into the $N^1$-hydroxyalkyl compound. Finally, hydrolysis of the 4-acetamide function leads to the target compound. The disadvantage of this process is that three reaction stages are carried out in mixtures of an organic solvent and water. This means that the solvents must be regenerated expensively. Moreover, the individual steps proceed with an unsatisfactory selectivity, so that only inadequate product purities are achieved.

It is also already known to prepare N-substituted nitro-p-phenylenediamines by reaction of 4-fluoro-3-nitroanilines with amines (for example U.S. Pat. No. 3,632,582, GB 1 206 491 and DE 17 68 999). To achieve as complete as possible a reaction, these processes operate with a large excess of amine. This causes considerable ecological problems, especially since regeneration of the excess amines is not worthwhile from the economic point of view. Moreover, these processes also produce products of inadequate purity and additionally comparatively low yields.

The object of the present invention is to provide a process for the preparation of N-substituted nitro-p-phenylenediamines which is acceptable from both the ecological and the economic aspect.

Surprisingly, this object is achieved by a process for the preparation of compounds of the general formula I

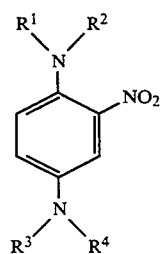

(I)

wherein
$R^1$ and $R^2$ independently of one another denote hydrogen, $(C_1-C_4)$-alkyl, $(C_1-C_4)$-hydroxyalkyl or $(C_5-C_6)$-cycloalkyl, or, together with the nitrogen atom carrying them, form $(C_4-C_6)$-heterocyclyl and
$R^3$ and $R^4$ independently of one another denote hydrogen, $(C_1-C_4)$-alkyl, $(C_1-C_4)$-hydroxyalkyl, $(C_1-C_2)$-alkylcarbonyl or tosyl, by reaction of a compound of the general formula II

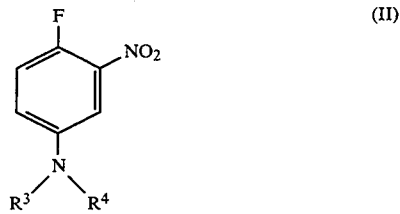

(II)

with an amine of the general formula III

(III)

wherein $R^1$, $R^2$, $R^3$ and $R^4$ are defined as stated above, characterised in that the reaction is carried out in the presence of an alkali metal hydroxide, and the amine of the general formula III is employed in amounts of 1.4 to 1.8 mol per mol of compound of the general formula II.

The $(C_1-C_4)$-alkyl groups mentioned can be straight-chain or branched and denote methyl, ethyl, i-propyl, n-propyl, n-butyl, i-butyl, sec-butyl and tert-butyl. The same applies analogously to the $(C_1-C_4)$-hydroxyalkyl groups mentioned, the hydroxyethyl, 3-hydroxypropyl and 2-hydroxypropyl groups being preferred. $(C_5-C_6)$-Cycloalkyl is preferably cyclohexyl. $(C_4-C_6)$-Heterocyclyl is preferably a cyclic ring containing a nitrogens particularly preferably pyrrolidinyl, piperidinyl or morpholinyl. $(C_1-C_2)$-Alkylcarbonyl is preferably represented by the acetyl group.

Preferred compounds of the general formula II are, for example, 4-fluoro-3-nitroaniline, N,N-bis-(2-hydroxyethy)-4-fluoro-3-nitroaniline, N-acetyl-4-fluoro-3-nitroaniline and N-tosyl-4-fluoro-3-nitroaniline. 4-Fluoro-3-nitroaniline and N,N-bis(2-hydroxyethyl)-4fluoro-3-nitroaniline are particularly preferred.

Preferred amines of the general formula III are, for example, ethanolamine, diethanolamine, 3-hydroxypropylamine, 2-hydroxypropylamine, methylamine, dimethylamine, ethylamine, i-propylamine, t-butylamine, cyclohexylamine, pyrrolidine, piperidine and morpholine. Ethanolamine, 2-hydroxypropylamine and 3-hydroxypropylamine are particularly preferred.

Preferred compounds of the general formula I are $N^1$-(2-hydroxyethyl)-2-nitro-1,4-phenylenediamine and $N^1,N^4,N^4$-tris-(2-hydroxyethyl)-2-nitro-1,4-phenylenediamine.

The alkali metal hydroxides are preferably potassium hydroxide and sodium hydroxide, which are advantageously employed in the form of their aqueous solutions, that is to say, for example, as 50% strength sodium hydroxide or potassium hydroxide solution.

The alkali metal hydroxides are preferably employed in amounts of 0.6 to 1.2, particularly preferably 0.7 to 1.1 mol, per mol of compound of the general formula II. They can be metered in continuously over a certain period of time or according to the pH. The pH is preferably kept between 8.5 and 9.5 here.

The amine of the general formula III is preferably employed in amounts of 1.5 to 1.7 mol per mol of compound of the general formula II.

Water is preferably employed as the reaction medium. It is particularly preferable here to employ the washwater of a previous reaction according to the invention as the reaction medium. This can be used without additional purification for at least five further reaction batches.

The reaction according to the invention is preferably carried out at temperatures between room temperature and 120° C., particularly preferably at 80°–100° C.

The starting compounds of the general formula II and the amines of the general formula III are known. They can be obtained commercially or prepared by known processes.

The process according to the invention produces the compounds of the general formula I in higher yields and in a higher purity than the processes of the prior art. This is all the more surprising, since, because of the use of an alkali metal hydroxide, a person skilled in the art would have expected replacement of the fluorine by hydroxyl, that is to say the formation of phenols. In the literature (Synth. Commun. 13 (1983) 233), the synthesis of nitrophenols by reaction of fluoronitrobenzenes with sodium hydroxide solution is in fact described. However, phenols are not formed in the reaction according to the invention.

EXAMPLE 1

156 g (1 mol) of 4-fluoro-3-nitroaniline and 97.6 g (1.6 mol) of ethanolamine are heated at 100° C. in 500 ml of water. When the colour of the mixture has changed from yellow to red, 64 g (0.8 mol) of 50% strength sodium hydroxide solution are metered in continuously for 5 hours, so that the pH is kept between 8.5 and 9.5. The mixture is stirred at 100° C. for a further hour and cooled to room temperature, and the precipitate formed is filtered off with suction and washed with 500 ml of water in several portions.

| | |
|---|---|
| Yield: | 90% (177 g of bronze-coloured crystals), |
| Melting point: | 121–123° C.; |
| Purity: | 95–96% (spectrophotometric determination) |
| Reaction volume: | 0.7 l/mol |
| Amount of waste | |
| water: | 0.7 l/mol |
| COD: | 42 g/l |

For comparison, Example 3 of U.S. Pat. No. 3,632,582 was reproduced and the following values were obtained here:

| | |
|---|---|
| Yield: | 73% |
| Melting point: | 118° C. |
| Purity: | 82% (spectrophotometric determination) |
| Reaction volume: | 1.3 l/mol |
| Amount of waste | |
| water: | 1.3 l/mol |
| COD: | 104 g/l |

EXAMPLE 2

122 g (0.5 mol) of N,N-bis(2-hydroxyethyl)-4-fluoro-3-nitroaniline and 48.8 g (0.8 mol) of ethanolamine are heated at 100° C. in 250 ml of water. When the colour of the mixture has changed from yellow to violet, 32 g (0.4 mol) of 50% strength sodium hydroxide solution are metered in continuously in the course of 5 hours so that the pH is kept between 8.5 and 9.5. The mixture is stirred at 100° C. for a further hour and cooled to 10° C., and the product is filtered off with suction and washed with 250 ml of water in several portions.

| | |
|---|---|
| Yield: | 85% (121 g), |
| Melting point: | 103–104° C.; |
| Purity: | 96% (spectrophotometric determination) |
| Reaction volume: | 0.7 l/mol |

For comparison, Example 14 of U.S. Pat. No. 3,632,582 was reproduced, and the following values were obtained:

| | |
|---|---|
| Yield: | 79% |
| Melting point: | 100–101° C. |
| Purity: | 94% (spectrophotometric determination) |
| Reaction volume: | 1.3 l/mol |

We claim:
1. Process for the preparation of compounds of the general formula I

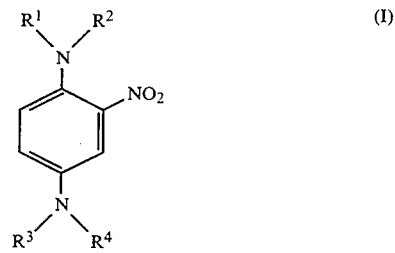

wherein
$R^1$ and $R^2$ independently of one another denote hydrogen, $(C_1-C_4)$-alkyl, $(C_1-C_4)$-hydroxyalkyl or $(C_5-C_6)$-cycloslkyl and
$R^3$ and $R^4$ independently of one another denote hydrogen, $(C_1-C_4)$-alkyl or $(C_1-C_4)$-hydroxyalkyl, by reaction of a compound of the general formula II

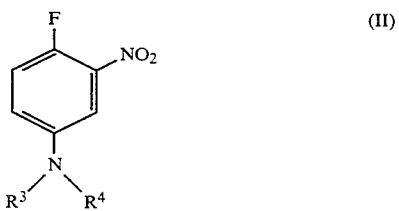

with an amine of the general formula III

wherein $R^1$, $R^2$, $R^3$ and $R^4$ are defined as stated above, comprising carrying out the reaction in the presence of an alkali metal hydroxide, and the amine of the general formula III is employed in mounts of 1.4 to 1.8 mol per tool of compound of the general formula II.

2. Process according to claim 1, wherein $N^1$-(2-hydroxyethyl)-2-nitro-1,4-phenylenediamine is prepared.

3. Process according to claim 1, wherein $N^1,N^4,N^4$-tris-(2-hydroxyethyl)-2-nitro-1,4-phenylenediamine is prepared.

4. Process according to claim 1, wherein potassium hydroxide or sodium hydroxide, in the form of their aqueous solutions, is employed as the alkali metal hydroxide.

5. Process according to claim 1, wherein water is employed as the reaction medium.

6. Process according to claim 5, wherein the washwater of a previous reaction is employed as the reaction medium.

7. Process according to claim 1, wherein $R^3$ and $R^4$ independently of one another denote hydrogen, hydroxyethyl, 3-hydroxypropyl, or 2-hydroxypropyl.

8. Process according to claim 1, wherein the compound of the general formula II is selected from the group consisting of 4-fluoro-3-nitroaniline, and N,N-bis-(2-hydroxyethyl)-4-fluoro-3-nitroaniline.

9. Process according to claim 8, wherein the compound of general formula II is 4-fluoro-3-nitroaniline or N,N-bis-(2-hydroxylethyl)-4-fluoro-3-nitroaniline.

10. Process according to claim 1, wherein the amine of formula III is selected from the group consisting of ethanolamine, diethanolamine, 3-hydmxypropylamine, 2-hydroxypropylamine, methylamine, dimethylamine, ethylamine, i-propylamine, t-butylamine and cyclohexylamine.

11. Process according to claim 10, wherein the amine of formula III is selected form the group consisting of ethanolamine, 2-hydroxypropylamine and 3-hydroxypropylamine.

12. Process according to claim 1, wherein the compound of general formula I is $N^1$-(2-hydroxyethyl)-2-nitro-1,4-phenylenediamine or $N^1,N^4,N^4$-tris-(2-hydroxyethyl)-2-nitro-1,4-phenylenediamine.

13. Process according to claim 1, wherein the alkali metal hydroxides are employed in amounts of 0.6 to 1.2 mol, per mol of compound of general formula II.

14. Process according to claim 1, wherein the alkali metal hydroxides are employed in amounts of 0.7 to 1.1 mol, per mol of compound of general formula II.

15. Process according to claim 1, wherein the reaction is carried out at a temperature between room temperature and 120° C.

16. Process according to claim 1, wherein the reaction is carried out at a temperature between 80° to 100° C.

17. Process according to claim 1, wherein the amine of general formula III is employed in amounts of 1.5 to 1.7 mol, per mol of compound of the general formula II.

18. The process according to claim 1, wherein the reaction is carried out at a temperature from 80° to 120° C.

19. The process according to claim 1, wherein in the reaction the pH is kept between 8.5 and 9.5.

* * * * *

UNITED STATES PATENT AND TRADEMARK OFFICE
CERTIFICATE OF CORRECTION

PATENT NO. : 5,414,128
DATED : May 9, 1995
INVENTOR(S) : Willi Steckelberg, et al.

It is certified that error appears in the above-indentified patent and that said Letters Patent is hereby corrected as shown below:

In column 2, line 38, the word "nitrogens" should read --nitrogen--

In column 2, line 46, the word "4fluoro-3-nitroaniline" should read --4-fluoro-3-nitroaniline--

In column 4, line 42, (claim 1) the word "cycloslkyl" should read --cycloalkyl--

In column 6, line 4, (claim 11) the word "form" should read --from--

Signed and Sealed this

Sixth Day of February, 1996

Attest:

BRUCE LEHMAN

Attesting Officer

Commissioner of Patents and Trademarks